United States Patent
Fries et al.

(10) Patent No.: US 11,323,251 B2
(45) Date of Patent: May 3, 2022

(54) METHOD AND SYSTEM FOR THE SECURE TRANSFER OF A DATASET

(71) Applicant: Siemens Healthcare GmbH, Erlangen (DE)

(72) Inventors: Steffen Fries, Baldham (DE); Ute Rosenbaum, Kempten (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 27 days.

(21) Appl. No.: 16/716,710

(22) Filed: Dec. 17, 2019

(65) Prior Publication Data

US 2020/0204361 A1 Jun. 25, 2020

(30) Foreign Application Priority Data

Dec. 20, 2018 (EP) ..................................... 18214594

(51) Int. Cl.
*H04L 9/08* (2006.01)
*G16H 30/40* (2018.01)
(Continued)

(52) U.S. Cl.
CPC ........... *H04L 9/0844* (2013.01); *G16H 30/40* (2018.01); *H04L 9/0861* (2013.01);
(Continued)

(58) Field of Classification Search
None
See application file for complete search history.

(56) References Cited

U.S. PATENT DOCUMENTS 8,782,774 B1 7/2014 Pahl et al.
9,887,839 B2 * 2/2018 Fadaie .................. H04L 63/061
(Continued)

FOREIGN PATENT DOCUMENTS

| CN | 105993146 A | 10/2016 |
|---|---|---|
| CN | 106161449 A | 11/2016 |
| CN | 106797311 A | 5/2017 |

OTHER PUBLICATIONS

Dong, Zheming et al. "Security Enhanced Anonymous Remote User Authentication and Key Agreement for Cloud Computing" IEEE 17th International Conference on Computational Science and Engineering, Dec. 19-21, 2014 // DOI: 10.1109/CSE.2014.320.
(Continued)

*Primary Examiner* — Jeffrey C Pwu
*Assistant Examiner* — Mayasa A. Shaawat
(74) *Attorney, Agent, or Firm* — Harness, Dickey & Pierce, P.L.C.

(57) ABSTRACT

A method for transfer of a dataset includes provisioning or generating a user-side Diffie Hellman key pair, including a secret user key and a public user key; transferring the public user key to the server; provisioning or generating a server-side Diffie Hellman key pair, including secret server and public server keys; provisioning a dataset on the server; generating a server-side Diffie Hellman key using the secret server key and the public user key, and encrypting the dataset to generate an encrypted dataset, via a resulting server-side Diffie Hellman key generated on the server side; transferring the encrypted dataset to the cloud service; retrieving the public server key and the encrypted dataset from the cloud service; and generating a user-side Diffie Hellman key using the secret user key and the public server key retrieved, and decrypting the encrypted dataset on the user device using the user-side Diffie Hellman key.

22 Claims, 4 Drawing Sheets

(51) Int. Cl.
  *H04L 9/32*   (2006.01)
  *H04L 29/06*  (2006.01)

(52) U.S. Cl.
  CPC .......... *H04L 9/3247* (2013.01); *H04L 9/3263* (2013.01); *H04L 9/3271* (2013.01); *H04L 63/0435* (2013.01); *H04L 63/168* (2013.01)

(56) References Cited

U.S. PATENT DOCUMENTS

| | | | |
|---|---|---|---|
| 2010/0211782 A1* | 8/2010 | Auradkar | H04L 9/083 |
| | | | 713/168 |
| 2012/0213370 A1* | 8/2012 | Moskovics | G06F 21/57 |
| | | | 380/278 |
| 2015/0067338 A1 | 3/2015 | Gero et al. | |
| 2016/0065370 A1* | 3/2016 | Le Saint | H04L 9/0841 |
| | | | 713/155 |
| 2016/0294548 A1* | 10/2016 | Qian | H04L 63/102 |
| 2017/0171178 A1 | 6/2017 | Reynders | |
| 2018/0167208 A1* | 6/2018 | Le Saint | H04L 63/0442 |

OTHER PUBLICATIONS

Standard DIN EN ISO 15118-1 "Road vehicles—Vehicle to grid communication interface" Edition Dec. 2015 // https://www.din.de/en/getting-involved/standards-committees/naautomobil/standards/wdc-beuth:din21:239464126?destinationLanguage=&sourceLanguage=.

European Search Report for the European Patent Application No. 18214594. dated Jun. 12, 2019.

Dierks, T. "The Transport Layer Security (TLS) Protocol." *RTFM, Inc.* (Aug. 2008).

\* cited by examiner

METHOD AND SYSTEM FOR THE SECURE TRANSFER OF A DATASET

PRIORITY STATEMENT

The present application hereby claims priority under 35 U.S.C. § 119 to European patent application number EP18214594.6 filed Dec. 20, 2018, the entire contents of which are hereby incorporated herein by reference.

FIELD

Embodiments of the invention generally relate to invention relates to a method and a system for the secure transfer of a dataset, in particular a medical dataset, between a server and a user device via a cloud service, and a corresponding medical system.

BACKGROUND

There are an increasing number of use cases where data services are used as cloud applications to realize access to data outside of a private, closed network or also to process data stored in the cloud. Relevant examples include the processing of measurement data by smart meters in the cloud, e.g. by a metering operator. A further example is the evaluation of parameters from imaging methods in the healthcare sector. In both cases, an anonymization or pseudo-anonymization of the data is required in order to make the reference to a specific person unrecognizable.

Various methods are known for transferring sensitive data, some of which are explained in more detail below.

A method known as "S/MIME" allows encrypted data to be sent by email. S/MIME is based here on two-stage encryption. The message itself is symmetrically encrypted to protect the confidentiality. The key used for this purpose is then encrypted (asymmetrically) with the public key of the recipient. This ensures that only the recipient who is also in possession of the corresponding private key can decrypt the email.

"RSA encryption" named after the initial letters of the surnames of the inventors allows data to be encrypted using the public key of a recipient. The asymmetric encryption used here is time-consuming, and consequently this results in combined methods (as described earlier with S/MIME) generally being used. RSA encryption is therefore used in particular for key management. One example is TLS (IETF RFC 5246), a security protocol which is frequently used with web-based applications.

The "Diffie Hellman key exchange" is a method for establishing a symmetric key which can then be used to protect mass data. In this case both the sender and the recipient each generate a key pair, the respective public keys of which can be published. The corresponding secret keys remain with the sender or the recipient. The sender can generate a message for the recipient using the public recipient key and the sender's secret sender key. The recipient can then extract the message using the public sender key and the recipient's secret recipient key. Furthermore certificates are known (ECDSA certificates), the public ECDSA key of which can be used at the same time as the public Diffie Hellman key.

A standard known under the designation "ISO/IEC 15118" describes a method for the communication exchange between a charging point and an electric vehicle. One part of the exchanged information comprises a key pair generated in the backend and which can be transported to the electric vehicle via a message. The vehicle has an ECDSA-based key pair which is known in the backend. In the backend the public key in the ECDSA certificate is handled as a static Diffie Hellman key. If the backend wants to transfer the centrally generated key pair securely to the electric vehicle it generates its own Diffie Hellman key pair and generates the Diffie Hellman secret from the public key of the electric vehicle and its own secret key and uses this to encrypt the key pair which is to be transported securely to the electric vehicle. The encrypted key pair and the public Diffie Hellmann key of the backend are then sent signed to the electric vehicle. The electric vehicle can then generate the Diffie Hellman secret via its private Diffie Hellman key and the public key of the backend, and decrypt and install the key pair. However, this solution only functions if both parties trust the underlying certificates which were used for the signature. This trust is generally achieved by a common certification authority or a certification authority which is trustworthy for both partners.

In the case of medical applications, it can be necessary however in individual cases to reverse the pseudo-anonymization of the data, for example in the event of extreme measurement values which mean that an analysis of the causes is essential. This re-identification may however only take place in the sphere of the data collection authority, an access option by the provider of the cloud application must be excluded. One example of this is increased radiation dosage values in the context of imaging methods in the hospital, the causes of which must be analyzed and documented also for regulatory reasons.

SUMMARY

The inventors have discovered that, according to the prior art, this cannot be efficiently and conveniently provided via typically used key distribution mechanisms for the distribution of symmetric keys for known encryption methods.

Embodiments of the present invention specify an alternative, more convenient method and a corresponding system as well as a medical system, with which one or more of the disadvantages described above are reduced or even avoided. In particular, at least one embodiment of the present invention provides a method which allows the patient-related data to be made available to a user in an encrypted form via a cloud service.

Embodiments of the present invention are achieved by a method, by a system and by a medical system.

Embodiments of the inventive method and the inventive system are typically used for the secure transfer of a (in particular medical) dataset between a server and a user device via a cloud service. However other applications, such as for example the transfer of other security-critical datasets, are of course also possible.

Cloud computing in the context of embodiments of the invention relates to the provision of storage space as a service via a network, in particular via the Internet. In this case, the storage space does not have to be installed on the local computer network of a medical facility, but can be sourced from one or more providers as required. The invention can be employed particularly advantageously if this storage space is outside of the medical facility in which the user device and the server are located and can only be achieved via an Internet connection (inherently deemed to be unsecure). Even though the term "cloud" comes from the English language, it can also be used in the German language for corresponding services. For better understanding, the terms "cloud" or "cloud service" are used below for a service which provides storage space and via which data can be saved to this storage space or can be retrieved therefrom.

At least one embodiment of the application is directed to a method for the secure transfer of a (in particular medical) dataset between a server and a user device via a cloud service, comprising:

provisioning or generating a user-side Diffie Hellman key pair, via the user device, including a secret user key and a public user key;

transferring the public user key to the server;

at least one of provisioning and generating a server-side Diffie Hellman key pair, via the server, including a secret server key and a public server key;

provisioning a dataset on the server;

generating a server-side Diffie Hellman key on the server, using the secret server key and the public user key, and encrypting the dataset on the server to generate an encrypted dataset, via a resulting server-side Diffie Hellman key generated on the server side;

transferring the encrypted dataset to the cloud service;

retrieving the public server key and the encrypted dataset from the cloud service, via the user device; and generating a user-side Diffie Hellman key on the user device by using the secret user key and the public server key retrieved, and decrypting the encrypted dataset on the user device using the user-side Diffie Hellman key.

At least one embodiment of the application is directed to a system, for secure transfer of a dataset between a server and a user device via a cloud service, comprising:

a server;

a user device;

a data connection between the server and the user device; and a data interface for a data connection between the server and the user device, with a cloud service, wherein the user device is designed to at least one of retrieve and generate a user-side Diffie Hellman key pair including a secret user key and a public user key, the system is designed to transfer the public user key to the server, the server is designed to at least one of retrieve and generate a server-side Diffie Hellman key pair including a secret server key and a public server key, the server is designed to retrieve a dataset, the server is designed to generate a server-side Diffie Hellman key using the secret server key and the public user key, and to encrypt the dataset, via the server-side Diffie Hellman key generated, to generate an encrypted dataset, the server is designed to transfer the encrypted dataset to the cloud service, the user device is designed to retrieve the public server key and to retrieve the encrypted dataset from the cloud service, and the user device is designed to generate a user-side Diffie Hellman key, using the secret user key and the retrieved public server key, and to decrypt the encrypted dataset on the user device with the user-side Diffie Hellman key generated.

At least one embodiment of the application is directed to a non-transitory computer program product, storing a computer program directly loadable into a memory storage facility of a medical system, the computer program including program sections to carry out the method of an embodiment when the computer program is executed in the medical system.

At least one embodiment of the application is directed to a non-transitory computer-readable medium, storing program sections readable in and executable by a computer unit, to carry out the method of an embodiment when the program sections are executed by the computer unit.

An inventive medical system of at least one embodiment is preferably configured to capture and/or to process medical images and is designed for integration as a server in a method of at least one embodiment. Alternatively or in addition the medical system comprises a server of an inventive system. The medical system therefore comprises a server which is designed:

to receive a public user key from a user system, to retrieve and/or generate a server-side Diffie Hellman key pair comprising a secret server key and a public server key, to retrieve a dataset, to generate a server-side Diffie Hellman key by using the secret server key and the public user key and to encrypt the dataset via the resulting server-side Diffie Hellman key, and to transfer the encrypted dataset to a cloud service.

A server of this type can however also be present independently of a medical system. An inventive server of an embodiment, which can be used in the context of an embodiment of the inventive method for the secure transfer of a dataset comprises at least:

a receiving unit designed to receive a public user key from a user system, a key unit designed to retrieve and/or generate a server-side Diffie Hellman key pair comprising a secret server key and a public server key, a data interface designed to retrieve a dataset, an encryption unit designed to generate a server-side Diffie Hellman key by using the secret server key and the public user key and to encrypt the dataset via the resulting server-side Diffie Hellman key, and a transfer unit designed to transfer the encrypted dataset to a cloud service.

An inventive server of at least one embodiment is therefore in a position to perform at least one embodiment of an inventive (server-side) method which comprises:

receiving a public user key from a user system, retrieving and/or generating a server-side Diffie Hellman key pair comprising a secret server key and a public server key, retrieving a dataset, generating a server-side Diffie Hellman key by using the secret server key and the public user key and to encrypt the dataset via the resulting server-side Diffie Hellman key, and transferring the encrypted dataset to a cloud service.

An inventive user device of at least one embodiment which can be used in the context of at least one embodiment of the inventive method for the secure transfer of a dataset comprises:

a data interface designed for a data connection to a server, a data interface designed for a data connection to a cloud service, a key unit designed to retrieve and/or generate a user-side Diffie Hellman key pair comprising a secret user key and a public user key, a sending unit designed to transfer the public user key to a server, a retrieval unit designed to retrieve the public server key and to retrieve an encrypted dataset from a cloud service, a decryption unit designed to generate a user-side Diffie Hellman key by using the secret user key and a retrieved public server key and to decrypt the encrypted dataset on the user device with the resulting user-side Diffie Hellman key.

An inventive user system of at least one embodiment is therefore in a position to perform an inventive (user-side) method which comprises:

retrieving and/or generating a user-side Diffie Hellman key pair comprising a secret user key and a public user key, transferring the public user key to a server, retrieving the public server key and retrieving an encrypted dataset from a cloud service, generating a user-side Diffie Hellman key by using the secret user key and a retrieved public server key and decrypting the encrypted dataset on the user device with the resulting user-side Diffie Hellman key.

An inventive system of at least one embodiment preferably comprises of at least one embodiment an inventive user device and of at least one embodiment an inventive server.

BRIEF DESCRIPTION OF THE DRAWINGS

The invention is explained once more in more detail below with reference to the appended figures on the basis of example embodiments. In the various figures, the same components are identified with identical reference signs. The figures are in general not to scale. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code.

Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the application is directed to a method for the secure transfer of a (in particular medical) dataset between a server and a user device via a cloud service, comprising:

provisioning or generating a user-side Diffie Hellman key pair, via the user device, including a secret user key and a public user key;

transferring the public user key to the server;

at least one of provisioning and generating a server-side Diffie Hellman key pair, via the server, including a secret server key and a public server key;

provisioning a dataset on the server;

generating a server-side Diffie Hellman key on the server, using the secret server key and the public user key, and encrypting the dataset on the server to generate an encrypted dataset, via a resulting server-side Diffie Hellman key generated on the server side;

transferring the encrypted dataset to the cloud service;

retrieving the public server key and the encrypted dataset from the cloud service, via the user device; and generating a user-side Diffie Hellman key on the user device by using the secret user key and the public server key retrieved, and decrypting the encrypted dataset on the user device using the user-side Diffie Hellman key, on the user side.

More specifically, these method limitations are discussed as follows:

Provision and/or generation of a user-side (first) Diffie Hellman key pair by the user device. This user-side Diffie Hellman key pair of course comprises a secret user key and a public user key. The principles of Diffie Hellman encryption are known to a person skilled in the art and are described in outline form in the introductory section. In the case of preferred encryption one key pair per request, one key pair per user or one key pair per queried server is generated or used. The term "generation" here means that a key pair is calculated, "provision" means making available a key pair which has already been calculated, e.g. from a data storage unit.

Transfer of the public user key to the server. In this context the public user key is sent via a data line from the user device to the server. As this usually takes place within a network of a medical facility, which is often outwardly secured from an IT perspective, a normal http connection can absolutely be used (http: "Hypertext Transfer Protocol"). However, even in this environment, at least on the server side secured connections via https are typically used. In this context, the server authenticates itself to the user.

Provision and/or generation of a server-side (second) Diffie Hellman key pair by the server. This server-side key pair of course comprises a secret server key and a public server key. Depending on the use case, it is preferable for an individual key pair comprising a public server key and a secret server key to be generated by the server per dataset and/or per user device. However, it can also be the case that the key pair was already generated previously and in this step the key pair is simply made available by retrieving it from a storage unit.

Provision of a dataset on the server. This dataset typically comprises patient-related data, in particular medical images or measurement results which are confidential.

Generation of a server-side Diffie Hellman key on the server by using the secret server key and the public user key, and encryption of the dataset on the server via the Diffie Hellman key on the server side as a result of this key generation. The dataset is preferably located on the server for encryption and can for example be retrieved from the server by a medical device or from a database. The dataset can however also have been stored on the server ever since the creation of the dataset.

Transfer of the encrypted dataset (and if applicable of the public Diffie Hellman server key) to the cloud service. This can take place for example by way of known methods and protocols for transferring data in networks. As the cloud service can often be accessed via the Internet, an Internet line (with the corresponding protocols) can also be used as a possible transfer channel.

Retrieval of the public server key and retrieval of the encrypted dataset from the cloud service via the user device. Of course, here the public server key of the respective key pair which was used to generate the encryption key for the relevant encrypted dataset is retrieved. Preferably this public server key was stored together with the encrypted dataset by the cloud service (in the cloud) and both elements are retrieved from the cloud service, but other variants are also conceivable depending on the use case. This is described in further detail below.

Generation of a user-side Diffie Hellman key on the user device by using the secret user key and the retrieved public server key, and decryption of the encrypted dataset on the user device via the Diffie Hellman key on the user side as a result of this key generation.

It should be noted here that the original dataset is always encrypted on the server side and the user always retrieves the encrypted dataset from the cloud using their user device. The encrypted dataset is therefore neither retrieved directly from the server by the user device nor is the dataset directly encrypted by the user device and sent to the cloud. In the context of the invention, a communication ("query") between the user device and the server is only necessary to transfer the public user key and if applicable to give notice that a certain dataset is to be stored in the cloud.

In addition, the step below preferably follows:
Provision of the (encrypted) dataset via the user device, wherein provision preferably includes displaying, storing and/or processing the dataset.

As a precautionary measure it should be noted that the sequence of the method steps is not fixed as defined here provided there are not any technical reasons which require a particular sequence. For example, the provision of the dataset can already take place before the generation of one or of both key pairs, similarly for example the server-side key pair can also be generated before the user-side key pair. It is essentially just important that the relevant components required for a step are available.

Contrary to the prior art, the known Diffie-Hellman encryption between two users is transformed into a 3-point communication in which a Diffie Hellman key negotiation is adapted in such a way that the resulting key, which was used for the encryption, can be restored again at a later stage.

One advantage of at least one embodiment of the invention is that in addition to the encrypted data, information relating to the decryption of the data is provided without the cloud service being in a position to decrypt the data itself via this information.

At least one embodiment of the invention advantageously allows the data in the cloud to be accessed from different networks, i.e. from different user devices (clients) without the server having to be accessible to all clients. Furthermore at least one embodiment of the inventive principle simplifies the infrastructure. The proposed approach facilitates on the server side a simpler management of certificates for the authentication as part of the https communication as the security of the data in the cloud service is largely ensured by the Diffie Hellman key generation.

At least one embodiment of the inventive system for the secure transfer of a (in particular medical) dataset between a server and a user device via a cloud service comprises a server, a user device and a data connection between the server and the user device and a data interface for a data connection between the server and the user device with a cloud service. The server and the user device are configured in a particular way in this context, as explained below in more detail.

The user device is designed to retrieve and/or generate a user-side Diffie Hellman key pair comprising a secret user key and a public user key.

The system is designed to transfer the public user key to the server. The data connection between the server and the user device is used for this purpose.

The server is designed to retrieve and/or generate a server-side Diffie Hellman key pair comprising a secret server key and a public server key. As already mentioned above, the server-side Diffie Hellman key pair can be sourced from a storage unit on the server or even from a database. This connection to the database should be secure or the server-side Diffie Hellman key pair should be transferred in encrypted form. It is particularly preferable if the server is configured both to generate a Diffie Hellman key pair and to retrieve a Diffie Hellman key pair (from a storage unit).

The server is designed to retrieve a dataset. This dataset can be sourced from a storage unit of the server or even from a database. This connection to the database should be secure or the dataset should be transferred in encrypted form. The server can be located in a medical device (a medical system) and medical data determined via this device, e.g. measurement results or images, can be encrypted directly according to at least one inventive principle (with at least one embodiment of the inventive method).

The server is designed to generate a server-side Diffie Hellman key by using the secret server key and the public user key and to encrypt the dataset via the resulting server-side Diffie Hellman key.

The server is designed to transfer the encrypted dataset to the cloud service.

The user device is designed to retrieve the encrypted dataset and the public server key from the cloud service.

The user device is designed to generate a user-side Diffie Hellman key by using the secret user key and the retrieved public server key and to decrypt the encrypted dataset on the user device with the resulting user-side Diffie Hellman key.

The user device is preferably also designed to provide the (encrypted) dataset, wherein the provision preferably includes displaying, storing and/or processing the dataset.

It should be noted that the system components mentioned above and described below (individual system components or each of the system components, i.e. server or user device or database) can include one or more of the following subcomponents, wherein each of these subcomponents can also include several interacting subcomponents:

a computing unit ("CPU"), in particular a computing unit of the group comprising processor, microprocessor, integrated circuit, GPU, ASIC, FPGA, a storage unit, in particular a storage unit of the group comprising magnetic storage (e.g. a hard disk), semi-conductor storage (e.g. a solid state disk), optical storage (e.g. DVD) or mixed forms of these data storage options, an interface (e.g. a data bus, a WLAN, a LAN or a USB interface).

An inventive medical system of at least one embodiment is preferably configured to capture and/or to process medical images and is designed for integration as a server in a method of at least one embodiment. Alternatively or in addition the medical system comprises a server of an inventive system. The medical system therefore comprises a server which is designed:

to receive a public user key from a user system, to retrieve and/or generate a server-side Diffie Hellman key pair comprising a secret server key and a public server key, to retrieve a dataset, to generate a server-side Diffie Hellman key by using the secret server key and the public user key and to encrypt the dataset via the resulting server-side Diffie Hellman key, and to transfer the encrypted dataset to a cloud service.

A server of this type can however also be present independently of a medical system. An inventive server of an embodiment, which can be used in the context of an embodiment of the inventive method for the secure transfer of a dataset comprises at least:

a receiving unit designed to receive a public user key from a user system, a key unit designed to retrieve and/or generate a server-side Diffie Hellman key pair comprising a secret server key and a public server key, a data interface designed to retrieve a dataset, an encryption unit designed to generate a server-side Diffie Hellman key by using the secret server key and the public user key and to encrypt the dataset via the resulting server-side Diffie Hellman key, and a transfer unit designed to transfer the encrypted dataset to a cloud service.

An inventive server of at least one embodiment is therefore in a position to perform at least one embodiment of an inventive (server-side) method which comprises:

receiving a public user key from a user system, retrieving and/or generating a server-side Diffie Hellman key pair comprising a secret server key and a public server key, retrieving a dataset, generating a server-side Diffie Hellman key by using the secret server key and the public user key and to encrypt the dataset via the resulting server-side Diffie Hellman key, and transferring the encrypted dataset to a cloud service.

An inventive user device of at least one embodiment which can be used in the context of at least one embodiment of the inventive method for the secure transfer of a dataset comprises:

a data interface designed for a data connection to a server, a data interface designed for a data connection to a cloud service, a key unit designed to retrieve and/or generate a user-side Diffie Hellman key pair comprising a secret user key and a public user key, a sending unit designed to transfer the public user key to a server, a retrieval unit designed to retrieve the public server key and to retrieve an encrypted dataset from a cloud service, a decryption unit designed to generate a user-side Diffie Hellman key by using the secret user key and a retrieved public server key and to decrypt the encrypted dataset on the user device with the resulting user-side Diffie Hellman key.

An inventive user system of at least one embodiment is therefore in a position to perform an inventive (user-side) method which comprises:

retrieving and/or generating a user-side Diffie Hellman key pair comprising a secret user key and a public user key, transferring the public user key to a server, retrieving the public server key and retrieving an encrypted dataset from a cloud service, generating a user-side Diffie Hellman key by using the secret user key and a retrieved public server key and decrypting the encrypted dataset on the user device with the resulting user-side Diffie Hellman key.

An inventive system of at least one embodiment preferably comprises of at least one embodiment an inventive user device and of at least one embodiment an inventive server.

A majority of the aforementioned components of the system may be realized entirely or partially in the form of software modules in a processor of a corresponding medical system. A realization largely through software has the advantage that conventionally used medical systems can also easily be upgraded with a software update in order to operate in the manner according to embodiments of the invention. In this respect, the object is also achieved by a corresponding computer program product comprising a computer program, which can be loaded directly into a computing system or a medical system and which contains program segments, in order to perform all the steps of the method according to an embodiment of the invention when the program is executed in the computing system or the medical system. Such a computer program product can comprise, where relevant, in addition to the computer program, further components, such as, for example, documentation and/or additional components including hardware components, for example, hardware keys (dongles, etc.) in order to use the software.

For transfer to the computing system and/or to the medical system, and/or for storage on, or in, the computing system and/or the medical system, a computer-readable medium, for instance a memory stick, a hard disk or any other portable or permanently installed data storage medium can be used, on which are stored the program segments of the computer program, which program segments can be downloaded and executed by a computing system and/or a processing unit of the medical system. For this, the processing unit can have, for example, one or more interacting microprocessors or the like.

Further, particularly advantageous embodiments and developments of the invention are given in the dependent claims and in the following description, where the claims in one category of claims can also be developed in a similar way to the claims and passages of the description in another category of claims, and in particular individual features of different example embodiments or variants can also be combined to create new example embodiments or variants.

It should be noted that the user should save and have on hand their secret user key for decrypting the dataset as otherwise they would no longer be in a position to reconstruct the key for decrypting the dataset based on the public server key. If a user generates a new key pair for each encryption process, they must consequently also retain all secret user keys. In this case it is however advantageous if they receive a notification as to which encrypted dataset in the cloud can be decrypted with which secret user key. For example, the dataset can include a corresponding note confirming which secret user key must be used (but without disclosing the user key). This problem is covered in further detail below.

In accordance with a preferred method the encrypted dataset is transferred to the cloud with the public server key. Following the transfer, the encrypted dataset and the public server key are preferably stored together in the cloud. The encrypted dataset and the public server key are also preferably stored together in the cloud with a reference to one another. This has the advantage that in the event of a retrieval by the user device the encrypted dataset and the public server key are sent together to the user device.

Theoretically it is possible for the public server key not to be sent to the cloud, but for example to be sourced from the server. In this case however it must be known to the user device which public server key was used to encrypt the encrypted dataset so that also in this case it is advantageous for the encrypted dataset and the public server key to be stored with a reference to one another. Alternatively the server can however also perform an assignment to an encrypted dataset on the basis of the requesting user.

Depending on the application it is preferable for the encrypted dataset to be digitally signed by the server together with the public server key. This then binds the public server key to the dataset.

In accordance with a preferred method in addition to the transfer of the public user key a user reference number is also transferred to the server by the user device. This user reference number is defined here in such a way as to allow conclusions to be drawn regarding the user and/or the user device. In the event of a large number of encrypted datasets in the cloud service this allows a very good assignment to the users or user devices which should have access to these datasets, and facilitates in particular an effective search.

The user reference number is preferably also transferred as part of the transfer of the encrypted dataset to the cloud service (by the server). Following the transfer, the encrypted dataset and the user reference number are preferably stored together in the cloud. The encrypted dataset and the user reference number are also preferably stored together in the cloud with a reference to one another. This has the advantage that the encrypted dataset and the user reference number are linked to one another and an association can be checked in the event of a retrieval or a search query by a user device.

The user reference number is primarily advantageous for associating the (encrypted) datasets with a user or user device. If a server sends encrypted datasets to the cloud service without a user reference number, it is more difficult for the cloud service to answer a query from a user device with the corresponding encrypted datasets.

The user reference number can be advantageously used for the aforementioned assignment of a secret user key to a retrieved encrypted dataset. The user can use this user reference number to link the corresponding query for a dataset to the user reference number. To this end (e.g. per dataset) one user key pair (user-side Diffie Hellman key pair) is preferably generated which is computationally linked with the user reference number (at least the secret user key) and then the public user key is sent to the server together with the user reference number and from this the encrypted dataset is stored together with the user reference number in the cloud. In the event of a retrieval the user reference number is available to the user device and the correct secret user key can be used.

Alternatively the user can reference the query only via the user reference number and can use a specific user key pair for all queries. A further alternative would be to use one user key pair per server to be queried. In this way all data queries could be linked with a server-specific user key, wherein a note is available in the cloud together with the encrypted dataset indicating which server encrypted the dataset.

The administration of all three alternatives lies with the user and can preferably be selected by the user. The URL to the encrypted dataset also preferably includes at least one part of the user reference number.

In accordance with a preferred method a previously generated key pair for a defined number of datasets and/or for a group of user devices is used by the server.

Theoretically this can be a single server-side key pair for all transactions from which the public server key can then be transferred directly to the user devices. This alternative is of course associated with a certain impairment of security. It is more secure if a different key pair is generated for each user device. Here too a single server-side key pair can theoretically be used for each user device and the public server key can be sent from the server to this user device and stored there. In this case a user reference number for the encrypted datasets would be very advantageous. In cases where the public server key arrived at the user system via another route than from the cloud service, a reference which indicates which public key is required to decrypt which dataset is very advantageous or even essential.

In accordance with a preferred method in the context of the retrieval of the encrypted dataset the dataset is retrieved together with the public server key by the user device from the cloud service, preferably indicating the user reference number. This is particularly advantageous if a (user-side) Diffie Hellman key pair is not generated for all user devices or respectively for one user device but a key pair is generated in relation to the datasets (e.g. a new one for each dataset). In this case the linking of a dataset to a user reference number is particularly advantageous.

The public key of the server is needed by the user device to decrypt an encrypted dataset. A group consisting of a dataset together with the public server key (of the key pair with which the key for encrypting the dataset was generated) simplifies the handling for the user device.

In accordance with a preferred method once the public user key has been transferred to the server this server performs an authentication of the user device. In the case of successful authentication the server then proceeds with making available or generating a (server-side) Diffie Hellman key pair. An authorization of the user device is preferably also checked.

The authentication preferably takes place by way of a challenge-response method. This is a knowledge-based user authentication method. One party presents a task (challenge) which the other party must resolve (response) in order to prove that they know specific information (shared secret) without transferring the actual information itself.

In accordance with a preferred method a key derivation is performed by way of a key derivation function before the dataset is encrypted by the server. Information and/or characteristics of the dataset designation preferably feed into the key derivation function, preferably a date (e.g. an MRT date in the case of magnetic resonance tomography images). The key derivation has the advantage that each dataset can be encrypted with a key which has been derived separately from a Diffie Hellman key.

The key derivation preferably takes place according to a method of the group comprising PBKDF (password-based key derivation function), HKDF (hash key derivation function), HMAC-SHA256 (hash-based message authentication code based on secure hash algorithm 256).

In accordance with a preferred method for the transfer of the encrypted dataset and preferably also of the public server key and/or of the user reference number the data connection between the server and the cloud service is initiated by the server and the cloud service authenticates itself via a certificate. It is therefore preferable that the server also authenticates itself with an individual proof of entitlement. Such a proof of entitlement is typically a combination of a username and a password or a certificate with the associated private key.

In accordance with a preferred method the transfer of the encrypted dataset to the cloud service and/or the retrieval of the encrypted dataset from the cloud service takes place via an http connection. An https connection, in other words an encrypted http connection (https: "Hypertext Transfer Protocol Secure"), is preferred between the cloud and the server and/or between the cloud and the user device. Theoretically the encryption of a connection could be dispensed with and simply an http connection used as the transferred dataset is already encrypted anyway. Having the that there is automatically an authentication of the communicating components as part of the https method. Without this man-in-the-middle attacks would be possible so that a third party could modify the data. In particular an attacker could change the association between the user reference number and the dataset and thus interchange the data of certain users. An https connection is therefore very advantageous.

In accordance with a preferred method the cloud service makes a publish/subscribe interface available to the user device. The user device preferably subscribes to the cloud service with regards to the desired encrypted dataset with the user reference number. In the software architecture publish/subscribe is a message template in the case of which a sender of messages (designated as a "Publisher") does not program the messages so that they are sent directly to certain recipients (so-called subscribers). Published messages are instead categorized into classes by the publisher without knowing which subscribers are available. Similarly subscribers register interest in one or more classes and receive only messages of interest to them without necessarily knowing which publishers are available.

In accordance with a preferred method the user device is informed as soon as the server has transferred the corresponding dataset to the cloud service.

Even if at first glance it would seem that a notification of the user is not necessary as the user initiated the transfer of the dataset to the cloud with the transfer of their public user key, it is still advantageous. For example it can be case that the user has queried several datasets via the server at different times and that the provision of the data takes place asynchronously. The user can then be informed if one of the queried datasets is available.

By way of at least one embodiment of the invention, person-related sensitive data can advantageously be made available via cloud services. The special feature here is that no separate certificates or publicly resolvable certificates have to be used on the user side for the authentication. This saves the user from having to configure the corresponding key material and also from ongoing management (renewal, etc.). In particular errors can be avoided if a user would like to use self-generated certificates instead of publicly resolvable certificates (from a public certification authority) in order to save costs. In this case the user device must first of all accept a certificate which cannot be checked. This process can represent a security risk. A particular advantage of the invention is that the information required for the decryption does not have to be provided by a public key infrastructure (PKI). This means that an additional configuration of the user device or the server is avoided.

Figure 1:
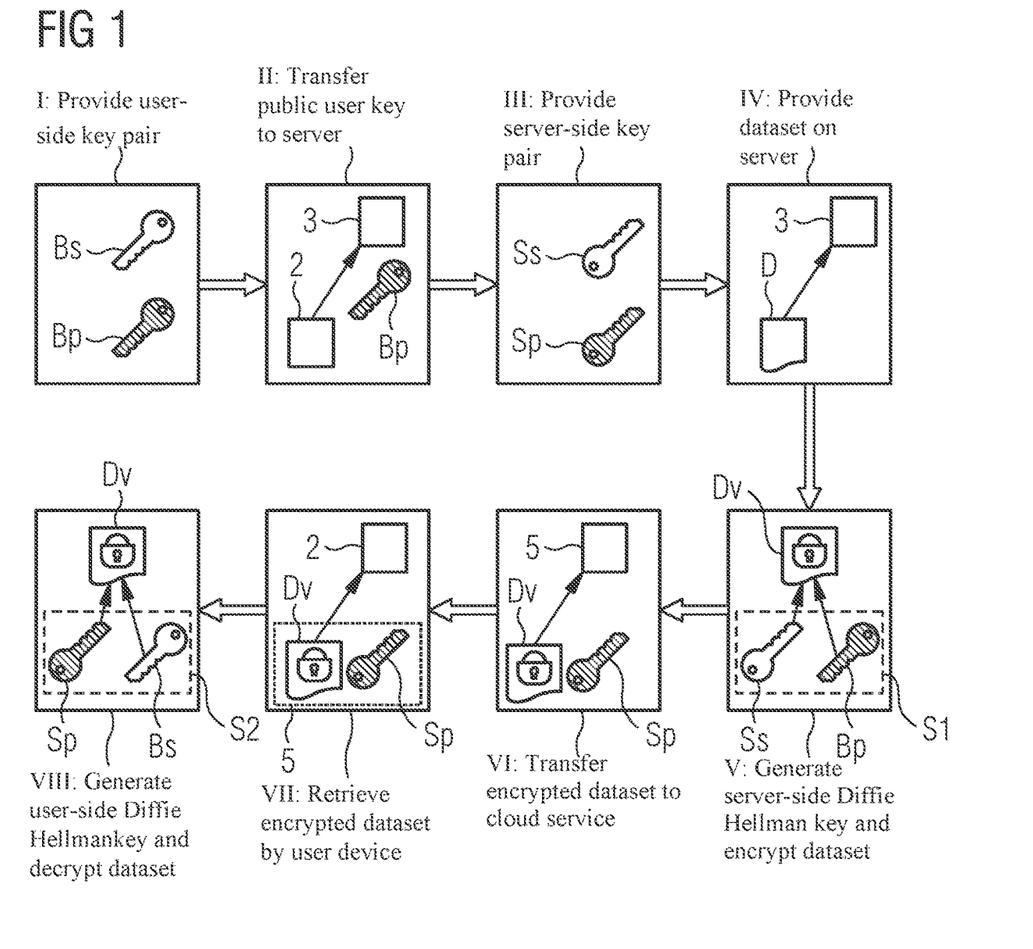
FIG. 1 shows a flow diagram for a possible workflow of an embodiment of an inventive method.

FIG. 1 shows a flow diagram for a possible workflow of an inventive method for the secure transfer of a (in particular medical) dataset D between a server 3 and a user device 2 via a cloud service 5. The method comprises the following steps:

In step I a user-side Diffie Hellman key pair Bp, Bs is provided or generated by the user device 2, comprising a secret user key Bs and a public user key Bp.

In step II the public user key Bp is transferred from the user device 2 to the server 3.

In step III a server-side Diffie Hellman key pair Sp, Ss is provided and/or generated by the server 3, comprising a secret server key Ss and a public server key Sp.

In step IV a dataset D is made available on the server 3. This is for example an image file.

In step V a server-side Diffie Hellman key S1 is generated on the server 3 by using the secret server key Ss and the public user key Bp and the dataset D on the server 3 is encrypted via the Diffie Hellman key S1 on the server side as a result of this key generation.

In step VI the encrypted dataset Dv is transferred to the cloud service 5. In this example the public server key Sp linked to the encrypted dataset Dv is also sent to the cloud service 5 and saved there together.

In step VII the public server key Sp is retrieved and the encrypted dataset Dv is retrieved from the cloud service 5 via the user device 2.

In step VIII a user-side Diffie Hellman key S2 is generated on the user device by using the secret user key Bs and the retrieved public server key Sp and the encrypted dataset Dv on the user device 2 is decrypted via the Diffie Hellman key S2 on the user side as a result of this key generation.

Figure 2:
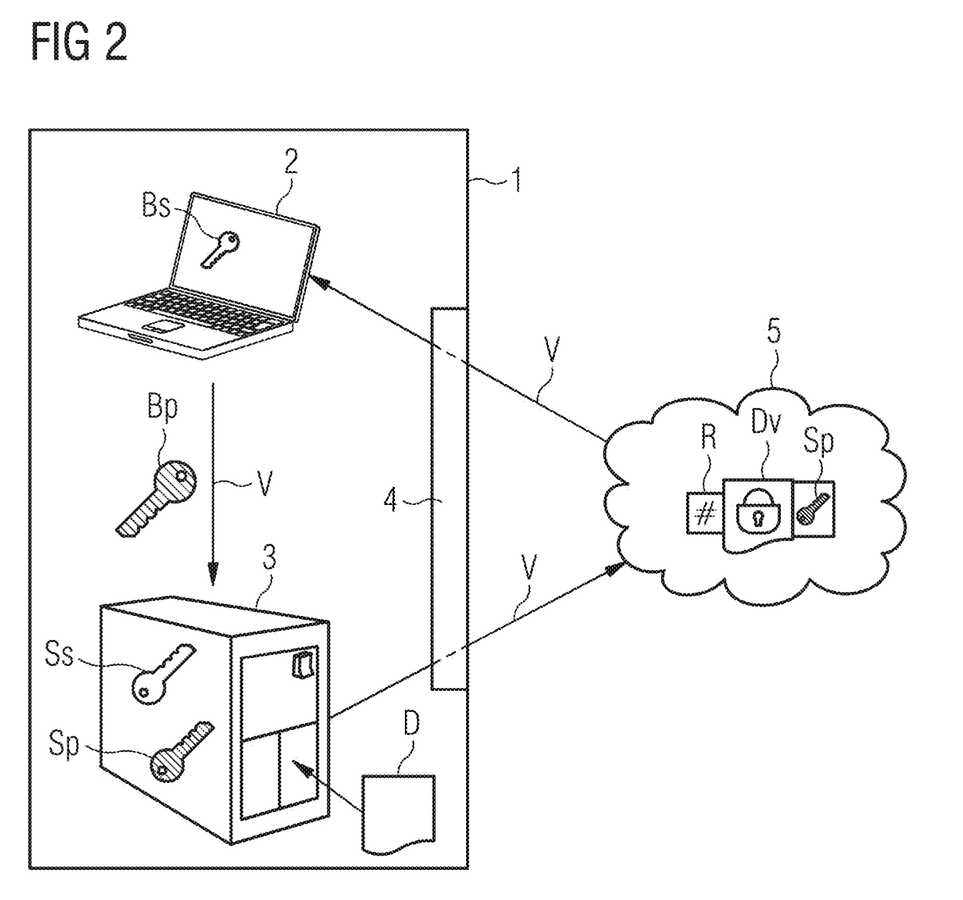
FIG. 2 shows a schematic example embodiment of an inventive system.

FIG. 2 shows a schematic example embodiment of an inventive system 1 for the secure transfer of a (in particular medical) dataset D between a server 3 and a user device 2 via a cloud service 5. The system 1 comprises a server 3, a user device 2 and a data connection V between the server 3 and the user device 2, as well as a data interface 4 for a data connection V between the server 3 and the user device 2 and a cloud service 5.

The user device 2 can for example be a computer with a network access and a browser. The server can be a web server which makes available the desired data. The system 1 in this case is part of the infrastructure within a hospital. The network of the hospital is generally restricted and the components operated within it (user device 2 and server 3) are generally restricted as regards the use of https certificates which can be publicly resolved as the distribution and maintenance of certificates and associated private keys with certificates which can be publicly resolved (by a trustworthy certification authority) is not possible. In the example shown a trustworthy environment is still assumed so an http connection can be used for the data connection V between the user device 2 and the server 3. Alternatively a separate certificate can however be installed which is configured as trusted by the user device and therefore also supports an https connection. A standard https connection can then be used as the data connection V to the cloud service.

The user device 2 is designed to retrieve and/or generate a user-side Diffie Hellman key pair Bp, Bs comprising a secret user key Bs and a public user key Bp.

The system 1 is designed to transfer the public user key Bp to the server 3. The scenario shown is one where the public user key Bp is transferred directly. For a better overview the public key is hatched and the secret key is white.

The server 3 is designed to retrieve and/or generate a server-side Diffie Hellman key pair Sp, Ss comprising a secret server key Ss and a public server key Sp. For better differentiation from the user keys Bp, Bs these are shown with the bit pointing upwards.

The server 3 is designed to retrieve a dataset D.

The server 3 is also designed to generate a server-side Diffie Hellman key S1 (see FIG. 1) by using the secret server key Ss and the public user key Bp and to encrypt the dataset D via the resulting server-side Diffie Hellman key S1. For a better overview an encrypted dataset Dv is shown with a padlock as can be seen in the cloud of the cloud service 5.

The server 3 is designed to transfer the encrypted dataset Dv to the cloud service 5. Furthermore in this example the server 3 is also designed to send a user reference number R to the cloud service 5. This has already happened here. The encrypted dataset Dv linked with the user reference number R and the public server key Sp can be seen in the cloud of the cloud service 5. In this example the same public server key Sp is always used.

The user device 2 is designed to retrieve the public server key Sp and to retrieve the encrypted dataset Dv from the cloud service 5.

The user device 2 is also designed to generate a user-side Diffie Hellman key S2 (see FIG. 1) by using the secret user key Bs and the retrieved public server key Sp and to decrypt the encrypted dataset Dv on the user device 2 with the resulting user-side Diffie Hellman key S2.

A data interface 4 can be a hardware or software interface (for example, Ethernet, PCI bus, USB or Firewire). A user device 2 or a server 3 can have hardware elements or software elements, for example a CPU ("central processing unit"), a GPU ("graphical processing unit"), a microprocessor, an FPGA ("field programmable gate array") or an ASIC ("application-specific integrated circuit"). A memory unit MU and/or a training memory unit TMU can be realized as a non-permanent working memory (random access memory, RAM) or as a permanent mass storage unit (hard disk, USB stick, SD card, solid state disk).

The data interface 4 can include in particular a plurality of subinterfaces which execute different steps of the respective methods. In other words the data interface 4 can also be regarded as a plurality of data interfaces 4. A user device 2 or a server 3 can include in particular a plurality of sub computing units which execute different steps of the respective methods. In other words the user device 2 and/or the server 3 can also be regarded as a plurality of the computing units.

Figure 3:
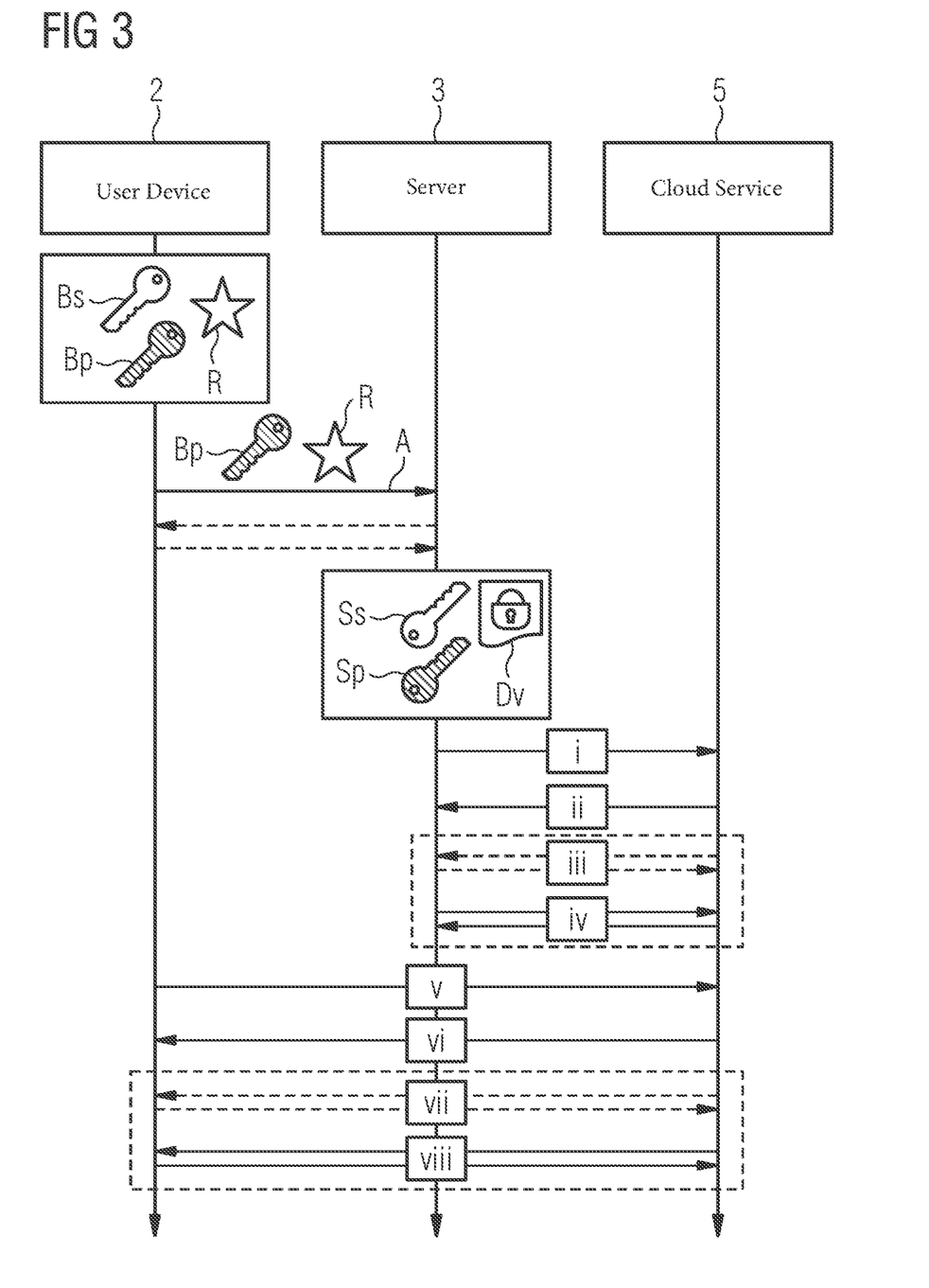
FIG. 3 shows a more detailed flow diagram for a possible workflow of an embodiment of an inventive method.

FIG. 3 shows a more detailed flow diagram for a possible workflow of an embodiment of an inventive method.

The user device 2 would like access to a certain dataset D (which is not yet located in the cloud) and to this end poses a query A to the server 3. Prior to this the user device generates a user-side Diffie Hellman key pair consisting of the public user key Bp, the secret user key Bs and a user reference number R.

The server 3 receives the query and carries out an authentication of the user device 2 (dotted arrows). This can for example be realized via a standard challenge-response method. If the authentication and also the authorization of the user device 2 is successful, the server 3 then generates a server-side Diffie Hellman key pair consisting of the public server key Sp and the secret server key Ss.

The server 3 is now in a position using the received public user key Bp and the secret server key Ss as described above to calculate a key and create an encrypted dataset Dv. Characteristics of the dataset designation can feed here into the key derivation function. This derivation has the advantage that each dataset can be encrypted with a separate key.

The server 3 then transfers the encrypted dataset Dv together with its public server key Sp and the user reference number R to the cloud service 5. The transport connection between the network-internal server 3 and the cloud service 5 is initiated by the server 3 (arrow 'i') and the cloud service 5 authenticates itself via a certificate (arrow 'ii'). The server in turn authenticates itself with a separate credential (arrow iii) which is usually a combination of username and password. The encrypted dataset Dv together with its public server key Sp and the user reference number R is then transferred by the server 3 followed by a message about the success on the part of the cloud service 5 (arrows iv).

A transport layer security connection (TLS connection) which is here established after the initiation (dashed box) is preferred.

The user device 2 can now pose a query to the cloud service 5 and set up a TLS connection in the same way as described above (arrows v and vi, dashed box). Within this connection the user device 2 can then transfer the user reference number R. In an alternative variant the cloud service makes available a publish/subscribe interface as indicated by the arrow pair vii. In this variant the user device can subscribe with the cloud service 5 to the event with the user reference number R. The cloud service 5 can now make available to the user device 2 the provided encrypted dataset Dv together with the public server key Sp (arrow pair viii).

Only the user device 2 which possesses the secret user key Bs is now in a position to calculate the matching key in order to decrypt the encrypted dataset Dv.

Figure 4:
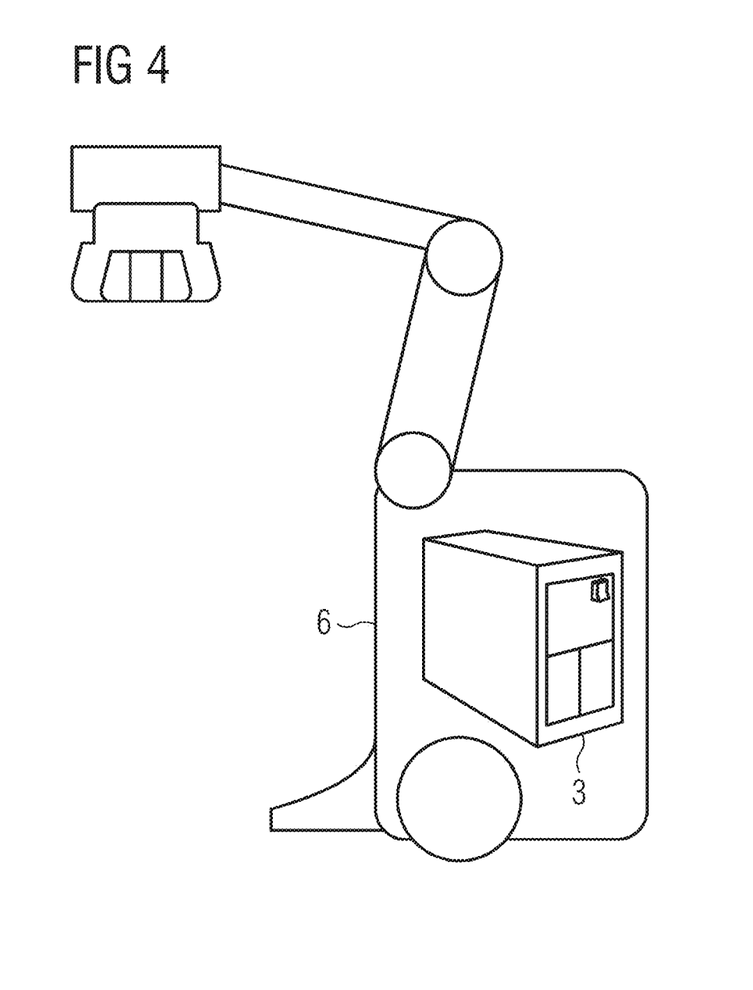
FIG. 4 shows a broadly schematic representation of a preferred medical system.

FIG. 4 shows a broadly schematic representation of a preferred medical system 6. This comprises a server 3 with a functionality as described above.

Finally it should be reiterated that the methods described in detail above and the presented system 1 are merely example embodiments which can be modified by a person skilled in the art in many ways without departing from the scope of the invention. In addition, the use of the indefinite article "a" or "an" does not preclude the relevant features also being present plurally. Similarly, the expressions "unit", "system" and "module" do not preclude the components in question from consisting of a plurality of cooperating partial components which can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for secure transfer of a dataset between a server and a user device via a cloud service, the method comprising:
  obtaining, by the user device, a user-side Diffie Hellman key pair including a secret user key and a public user key;
  obtaining, by the server, a server-side Diffie Hellman key pair including a secret server key and a public server key;
  generating a server-side Diffie Hellman key on the server using the secret server key and the public user key;
  encrypting a dataset on the server using the server-side Diffie Hellman key to obtain an encrypted dataset;
  transferring the encrypted dataset to the cloud service;
  retrieving, by the user device, the public server key and the encrypted dataset, the encrypted dataset being retrieved from the cloud service;
  generating a user-side Diffie Hellman key on the user device using the secret user key and the public server key; and
  decrypting the encrypted dataset on the user device using the user-side Diffie Hellman key.

2. The method of claim 1, further comprising:
  transferring the encrypted dataset and the public server key to the cloud service.

3. The method of claim 1, further comprising:
  transferring, by the user device, a user reference number to the server.

4. The method of claim 1, wherein the server-side Diffie Hellman key pair corresponds to at least one of a plurality of datasets and a group of user devices.

5. The method of claim 1, wherein the retrieving retrieves both the encrypted dataset and the public server key from the cloud service.

6. The method of claim 1, further comprising:
  performing, by the server, authentication of the user device in response to receiving the public user key from the user device,
  wherein the obtaining a server-side Diffie Hellman key pair obtains the server-side Diffie Hellman key pair in response to the authentication of the user device being successful, the authentication of the user device being based on a challenge-response method.

7. The method of claim 1, further comprising:
  performing a key derivation before the encrypting, the key derivation being based on the dataset and using a PBKDF, a HKDF, or HMAC-SHA256.

8. The method of claim 1, wherein
  the transferring the encrypted dataset is initiated by the server; and
  the transferring the encrypted dataset includes,
    authenticating the cloud service via a certificate, and
    authenticating the server with an individual proof of entitlement.

9. The method of claim 1, wherein at least one of the transferring the encrypted dataset or the retrieving the encrypted dataset is performed via an https connection.

10. The method of claim 1, further comprising:
  subscribing, by the user device, to a publish/subscribe interface with the cloud service corresponding to the encrypted dataset, the encrypted dataset corresponding to a user reference number.

11. The method of claim 1, further comprising:
  informing the user device of the transferring the encrypted dataset after transferring the encrypted dataset.

12. A system for secure transfer of a dataset between a server and a user device via a cloud service, the system comprising:
  a server;
  a user device connected to the server; and
  a data interface between a cloud service and both of the server and the user device, wherein
    the user device is configured to obtain a user-side Diffie Hellman key pair including a secret user key and a public user key,
    the server is configured to,
      obtain a server-side Diffie Hellman key pair including a secret server key and a public server key,
      generate a server-side Diffie Hellman key using the secret server key and the public user key,
      encrypt the dataset using the server-side Diffie Hellman key to obtain an encrypted dataset, and
      transfer the encrypted dataset to the cloud service, and
    the user device is configured to,
      retrieve the public server key and the encrypted dataset, the encrypted dataset being retrieved from the cloud service,
      generate a user-side Diffie Hellman key using the secret user key and the public server key, and
      decrypt the encrypted dataset with the user-side Diffie Hellman key.

13. A medical system for capture or processing of medical images, comprising:
  the server of the system of claim 12.

14. A non-transitory computer program product, storing a computer program directly loadable into a memory storage facility of a medical system, the computer program including program sections to carry out a method when the computer program is executed in the medical system, the method comprising:
- obtaining, by a user device, a user-side Diffie Hellman key pair including a secret user key and a public user key;
- obtaining, by a server, a server-side Diffie Hellman key pair including a secret server key and a public server key;
- generating a server-side Diffie Hellman key on the server using the secret server key and the public user key;
- encrypting a dataset on the server using the server-side Diffie Hellman key to obtain an encrypted dataset;
- transferring the encrypted dataset to a cloud service;
- retrieving, by the user device, the public server key and the encrypted dataset, the encrypted dataset being retrieved from the cloud service;
- generating a user-side Diffie Hellman key on the user device using the secret user key and the public server key; and
- decrypting the encrypted dataset on the user device using the user-side Diffie Hellman key.

15. A non-transitory computer-readable medium storing program sections that, when executed by a computer unit, cause the computer unit to perform a method, the method comprising:
- obtaining, by a user device, a user-side Diffie Hellman key pair including a secret user key and a public user key;
- obtaining, by a server, a server-side Diffie Hellman key pair including a secret server key and a public server key;
- generating a server-side Diffie Hellman key on the server using the secret server key and the public user key;
- encrypting a dataset on the server using the server-side Diffie Hellman key to obtain an encrypted dataset;
- transferring the encrypted dataset to a cloud service;
- retrieving, by the user device, the public server key and the encrypted dataset, the encrypted dataset being retrieved from the cloud service;
- generating a user-side Diffie Hellman key on the user device using the secret user key and the public server key; and
- decrypting the encrypted dataset on the user device using the user-side Diffie Hellman key.

16. The method of claim 2, wherein the encrypted dataset and the public server key are stored at least one of:
- together in the cloud service; or
- in reference to one another.

17. The method of claim 2, further comprising:
- digitally signing, by the server, the encrypted dataset and the public server key.

18. The method of claim 16, further comprising:
- digitally signing, by the server, the encrypted dataset and the public server key.

19. The method of claim 3, wherein the transferring the encrypted dataset transfers the encrypted data set and the user reference number to the cloud service.

20. The method of claim 19, wherein the user reference number and the encrypted dataset are stored at least one of:
- together in the cloud service; or
- in reference to one another.

21. The method of claim 1, wherein
- the transferring the encrypted dataset transfers the encrypted dataset from the server to the cloud service via a data interface; and
- the retrieving the encrypted dataset retrieves the encrypted dataset from the cloud service via the data interface.

22. The method of claim 1, wherein the cloud service is unable to decrypt the encrypted dataset.

* * * * *